US007887827B2

(12) United States Patent
Werk et al.

(10) Patent No.: US 7,887,827 B2
(45) Date of Patent: Feb. 15, 2011

(54) USE OF MALONOMICIN AND ANALOGS IN FUNGICIDAL APPLICATIONS

(75) Inventors: Todd Lowell Werk, Zionsville, IN (US); Carl Evan Snipes, Carmel, IN (US); Paul Richard Graupner, Carmel, IN (US); Cathy Lynn Peacock, Westfield, IN (US); Eleanor Lougee Chapin, Steep Falls, ME (US); William Kirkland Brewster, Indianapolis, IN (US); Frederick Richard Green, III, Noblesville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 449 days.

(21) Appl. No.: 11/795,829

(22) PCT Filed: Jan. 20, 2006

(86) PCT No.: PCT/US2006/002089

§ 371 (c)(1),
(2), (4) Date: Jul. 20, 2007

(87) PCT Pub. No.: WO2006/078939

PCT Pub. Date: Jul. 27, 2006

(65) Prior Publication Data
US 2008/0096956 A1 Apr. 24, 2008

(51) Int. Cl.
*A01N 25/00* (2006.01)
*A01N 43/36* (2006.01)
(52) U.S. Cl. ................................ 424/405; 514/408
(58) Field of Classification Search ................ None
See application file for complete search history.

(56) References Cited

U.S. PATENT DOCUMENTS 3,536,811 A * 10/1970 Ottens et al. ................ 424/116

OTHER PUBLICATIONS

Schipper et al Biosynthesis of Maonomycin—J. of The Chemical Society, Perkin Transactions 1: organic & ABio organic chemistry 1979 (8) pp. 2017-2022.*

* cited by examiner

*Primary Examiner*—Neil Levy
(74) *Attorney, Agent, or Firm*—Charles W. Arnett

(57) ABSTRACT

The present invention is related to the use of malonomicin compounds and derivatives in fungicidal applications and to new derivatives of malonomicin.

4 Claims, No Drawings

USE OF MALONOMICIN AND ANALOGS IN FUNGICIDAL APPLICATIONS

The invention is related to the field of compounds having fungicidal activity and their use in fungicidal applications.

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield and the quality of the crop and consequently, increase the value. However, no one fungicide is useful in all situations. Consequently, research is being conducted to produce fungicides that have better performance, that are easier to use, and that cost less.

Malonomicin or {[(2S)-2-amino-3-hydroxypropanoyl]amino}{2-[(5S)-5-(aminomethyl)-4-hydroxy-2-oxo-2,5-dihydro-1H-pyrrol-3-yl]-2-oxoethyl}malonic acid is a natural compound prepared by fermentation methods and is known for anti-protozoal activity. U.S. Pat. No. 3,536,811 discloses malonomicin used as antibiotics and inhibitors of protozoan growth.

The present invention relates to the use of compounds of Formula I:

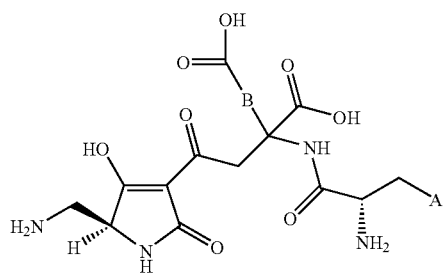

wherein B is either a bond or an alkylene group, and A is either OH or H; in fungicide applications. Formula I In one embodiment, the present invention relates to the use of the compound represented by the formula:

Compound I

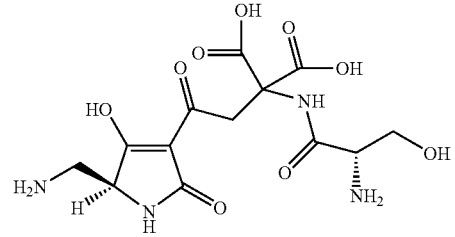

in fungicide applications.

In general, malonomicin can be produced by cultivating under controlled conditions an organism belonging to the genus *Streptomyces* which has been isolated from a soil sample from, for example the Black Forest of Germany. General methods of this type are described in U.S. Pat. No. 3,536,811, which is incorporated herein by reference, or synthesis as described in *The Total Synthesis of the Antibiotic Malonomicin* (K16) Tetrahedron. Vol. 34, pp. 223 to 231.

Various analogs of malonomicin can be synthesized by suitable modifications of the synthesis referenced above as described in the following examples.

One embodiment of the present invention is the use of a compound of Formula I, for protection of a plant against attack by a phytopathogenic organism or the treatment of a plant infested by a phytopathogenic organism, comprising applying a compound of Formula I to soil, a plant, a part of a plant, foliage, and/or seeds.

Throughout the specification, reference to the compounds of Formula I is read as also including ionic versions thereof, isomeric versions thereof, tautomeric versions thereof, or salts thereof. Exemplary salts include metal and amine salts, such as zinc and ammonium salts and the like.

In Formula I:

Formula I

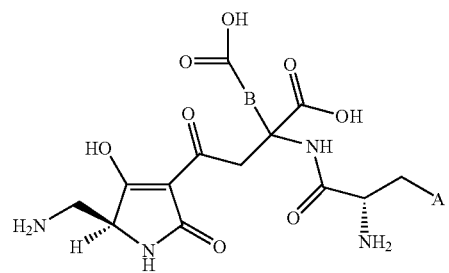

B is defined as either a bond or an alkylene group, and A is defined as either OH or H.

The term alkylene refers to a branched or unbranched $C_1$-$C_6$ alkyl bridging group, such as —$CH_2$—, —$CH_2$—$CH_2$—, and the like.

Specific embodiments of Formula I include the following:

Compound I

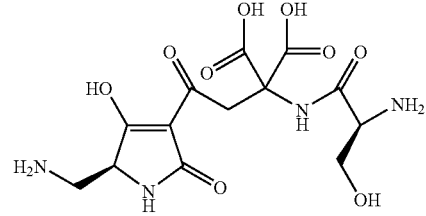

Compound II

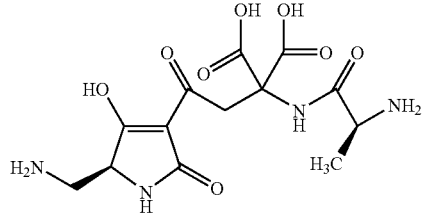

Compound III

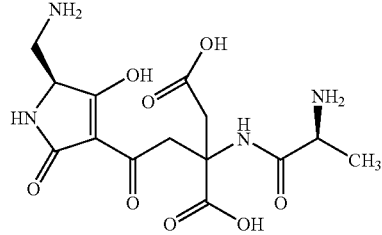

-continued

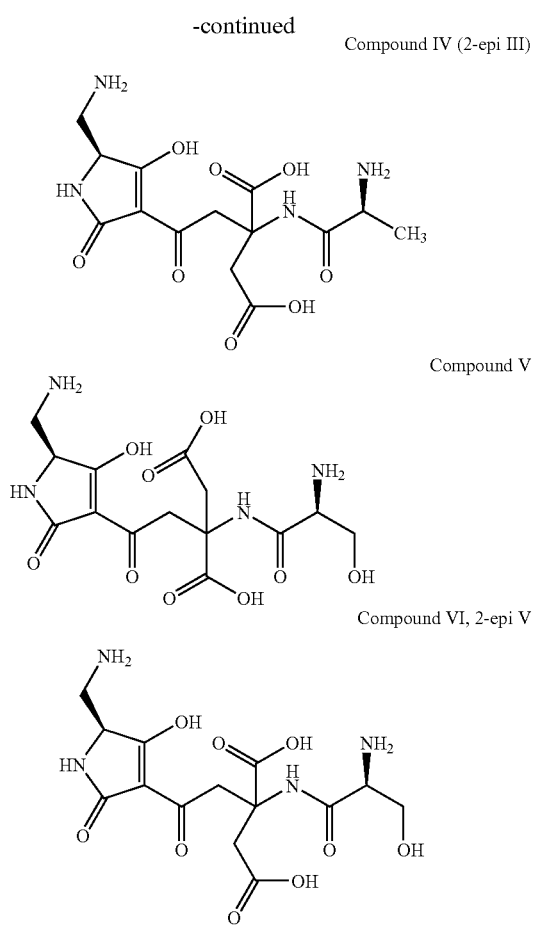

Compound IV (2-epi III)

Compound V

Compound VI, 2-epi V (Compound IV is the epimeric structure of Compound III and Compound VI is the epimeric structure of Compound VI.)

Additionally, another embodiment of the present invention is a composition useful for protecting a plant against attack by a phytopathogenic organism and/or treatment of a plant infested by a phytopathogenic organism comprising a compound of Formula I and a phytologically acceptable carrier material. Phytologically acceptable carriers include any material which can be combined with a compound of Formula I which helps enable the distribution of the compound on a plant or locus of a plant, without detrimental effect. Typical carriers include liquids, such as water and solvents and solids such as powders and dusts.

The compounds are applied by any of a variety of known techniques, either as the compounds or as formulations comprising the compounds. For example, the compounds may be applied to the roots, seeds or foliage of plants for the control of various fungi, without damaging the commercial value of the plants. The materials are applied in the form of any formulation types, including for example, but not limited to solutions, dusts, wettable powders, flowable concentrates, or emulsifiable concentrates.

Preferably, the compounds of the present invention are applied in the form of a formulation, comprising one or more of the compounds of Formula I with a phytologically acceptable carrier. Concentrated formulations can be dispersed in water, or other liquids, for application, or formulations can be dust-like or granular, which can then be applied without further treatment. The formulations can be prepared according to procedures that are conventional in the agricultural chemical art.

The present invention contemplates all vehicles by which one or more of the compounds can be formulated for delivery and use as a fungicide. Typically, formulations are applied as aqueous suspensions or emulsions. Such suspensions or emulsions are produced from water-soluble, water suspendable, or emulsifiable formulations which are solids, usually known as wettable powders; or liquids, usually known as emulsifiable concentrates, aqueous suspensions, or suspension concentrates. As will be readily appreciated, any material to which these compounds can be added may be used, provided they yield the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder is usually from 10 percent to 90 percent by weight based on the total weight of the wettable powder, more preferably 25 wt. percent to 75 wt. percent. In the preparation of wettable powder formulations, the compounds can be compounded with any finely divided solid, such as prophyllite, talc, chalk, gypsum, Fuller's earth, bentonite, aftapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I comprise a convenient concentration, such as from 10 wt. percent to 50 wt. percent of the compound, in a suitable liquid, based on the total weight of the concentrate. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulfated polyglycol ethers and appropriate salts of phosphated polyglycol ether.

Representative organic liquids which can be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Preferred organic liquids include xylene, and propyl benzene fractions, with xylene being most preferred. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I or salts thereof, dispersed in an aqueous vehicle at a concentration in the range from 5 to 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The compounds of Formula I or salts thereof, can also be applied as granular formulations, which are particularly useful for applications to the soil. Granular formulations usually contain from 0.5 to 10 wt. percent, bases on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from 0.5 to 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I can be prepared by intimately mixing one or more of the compounds in powdered form with a suitable dusty agricultural carrier, such as, for example, kaolin clay, ground volcanic rock, and the like. Dusts can suitably contain from 1 to 10 wt. percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The compounds of the present invention can also be combined with other fungicides, such as those listed in the *E-Pesticide Manual*, 12$^{th}$ Ed. Version 2.0, to form fungicidal mixtures or synergistic mixtures thereof. The fungicidal compounds of the present invention are often applied in conjunction with one or more other fungicides to control a wider variety of undesirable diseases. When used in conjunction with other fungicide(s), the presently claimed compounds can be formulated with the other fungicide(s), tank mixed with the other fungicide(s) or applied sequentially with other fungicide(s). Such other fungicides include 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, meta m-ammonium, metam-potassium, metam-sodium, metaminostrobin, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, *Reynoutria sachalinensis* extract, silthiofam, simeconazole, sodium 2-phenylphenoxide, sodium bicarbonate, sodium pentachlorophenoxide, spiroxamine, sulfur, SYP-Z071 (enestrobin), tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Tricho-*

*derma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril, benzamacril-isobutyl, benzamorf, binapacryl, bis-(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafaramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, farcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, muco-chloric anhydride, myclozolin, N-3,5-dichlorophenyl-succinimide, N-3-nitrophenylitaconimide, natamycin, N-ethylmercurio-4-toluene-sulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlor-fenphim, thiophanate, thioquinox, tioxymid, triamiphos, triarimol, triazbutil, trichlamide, urbacid, XRD-563, and zarilamid, and any combinations thereof.

Additionally, the compounds of the present invention can be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present invention are often applied in conjunction with one or more other pesticides to control a wider variety of undesirable pests. When used in conjunction with other pesticides, the presently claimed compounds can be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxy-carboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxy-fenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethyl-vinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organo-thiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion, fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyri-prole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, betacyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spiromesifen; thiourea insecticides such as diafenthiuron; urea insecticides such as flucofuron and sulcofuron; and unclassified insecticides such as closantel, crotamiton, EXD, fenazaflor, fenoxacrim, flubendiamide, hydramethylnon, isoprothiolane, malonoben, metaflumizone, metoxadiazone, nifluridide, pyridaben, pyridalyl, rafoxanide, triarathene and triazamate, and any combinations thereof.

The compounds of Formula I, or salt thereof, and the pesticidal compound in the combination can generally be present in a weight ratio of from 1:100 to 100:1.

Another embodiment of the present invention is a method for the control or prevention of fungal attack. This method comprises applying to the soil, plant, roots, foliage, seed or locus of the fungus, or to a locus in which the infestation is to be prevented, a fungicidal effective amount of one or more of the compounds of Formula I. The compounds are suitable for treatment of various plants at fungicidal levels, while exhibiting low phytotoxicity. The compounds are useful both in a protectant and/or an eradicant fashion.

The compounds have been found to have significant fungicidal effect particularly for agricultural use. Many of the compounds are particularly effective for use with agricultural crops and horticultural plants.

In particular, the compounds effectively control a variety of undesirable fungi that infect useful plant crops. Activity has been demonstrated for a variety of fungi, including for example the following representative fungi species: Downy Mildew of Grape (*Plasmopara viticola*-PLASVI); Late Blight of Tomato (*Phytophthora infestans*-PHYTIN); Brown Rust of Wheat (*Puccinia recondita* f. sp. *tritici*-PUCCRT); Glume Blotch of Wheat (*Leptosphaeria nodorum*-LEPTNO); Speckled Leaf Blotch of Wheat (*Septoria tritici*-SEPTTR); Powdery Mildew of Wheat (*Erysiphe graminis* f. sp. *tritici*-ERYSGT); Apple Scab (*Venturia inaequalis*-VENTIN); and Cucumber Anthracnose (*Colletotricum lagenarium*-COLLLA).

It will be understood by those in the art that the efficacy of the compound for the foregoing fungi establishes the general utility of the compounds as fungicides.

The compounds have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease inhibiting and phytologically acceptable amount" refers to an amount of a compound that kills or inhibits the plant disease for which control is desired, but is not significantly toxic to the plant. This amount will generally be from 1 to 1000 ppm (parts per million), with 10 to 500 ppm being preferred. The exact concentration of compound required varies with the fungal disease to be controlled, the type of formulation employed, the method of application, the particular plant species, climate conditions, and the like. A suitable application rate is typically in the range from 0.10 to 4 pounds/acre (0.01 to 0.45 grams per square meter $g/m^2$).

Another aspect of the present invention relates to new malonomicin derivatives represented by Compounds II, III, IV, V and VI as described previously.

The following examples are provided to illustrate the present invention. The examples are not intended to limit the scope of the present invention and they should not be so interpreted. Amounts are in weight parts or weight percentages unless otherwise indicated.

EXAMPLES

These examples are provided to further illustrate the invention and are not meant to be construed as limiting.

As disclosed herein, all temperatures are given in degrees Celsius and all percentages are weight percentages, except for percent yields which are mole percentages, unless otherwise stated.

I. Preparation of Compound I

A. Culture of the Producing Organism.

Culture CP 1391 was isolated from a soil sample collected in Guatemala. It was maintained on Bennett's agar composed of: 1.0 grams (g) yeast extract, 1.0 g Beef Extract, 2.0 g N-Z Amine Type A (Sheffield Chem. Co.), 10 g glucose, 15.0 g Bacto agar, and 1 L deionized water. The colonies on Bennett's were white with yellow edges, very large, raised, and wrinkled. Colonies from freshly sporulated agar cultures were transferred to 4 tri-baffled 250 milliliter (mL) flasks containing 50 mL vegetative media in each. The Yz strength N-Z Amine seed media is composed of: 5.0 g glucose, 10.0 g soluble starch, 2.5 g yeast extract, 2.5 g N-Z Amine Type A (Sigma), 0.5 reagent grade $CaCO_3$, and 1 L deionized water. The vegetative cultures were incubated at 30° C. on a New Brunswick G-25 rotary shaker at 150 rpm for 3 days. Tri-baffled wide mouth Fembach flasks containing 2800 mL Medium I growth media were inoculated with 5 mL of 3 day old vegetative culture. The Medium I media contained: 5 g corn steep powder, 5 g dextrose, 50 g lactose, 10 g soybean flour Nutrisoy, 5 g Bacto peptone, 3 g $CaCO_3$, 2 g $NH_4SO_4$, 0.1 g $FeCl_2{:}4H_2O$, 0.1 g $ZnCl_2$, 0.1 g $MnCl_2{:}4H_2O$, 0.5 g $MgSO_4{.}7H_2O$, and 1 L deionized water. The pH was adjusted to 7. The Fembach flasks were incubated on a New Brunswick G-25 rotary shaker at 150 rpm for 7 days at 30° C. The cultures were harvested on day 7.

B. Purification of Malonomicin From CP 1391 Broth

Malonomicin was purified by a method adapted from U.S. Pat. No. 3,536,811 on malonomicin and a paper describing the synthesis of malonomicin (Van der Baan et. al., Tetrahedron. 34: 223-231 (1978)). The whole culture was centrifuged for 15 minutes (min.) in one liter bottles at approximately 2500×G. The supernatant was filtered through a 0.22 micron filter. One liter of the filtrate was passed through a 40×200 mm column of Amberlite IRA-402 ion exchange resin (450 g) in the hydroxide form. After washing with 200 mL purified water, malonomicin was eluted with 250 mL 5 M acetic acid containing 1.5 percent ammonium acetate, followed by 250 mL purified water. The eluate was concentrated to 20 mL on a rotary evaporator, and the concentrate was added to 80 mL methanol to precipitate the malonomicin. The suspension was centrifuged at 2500×G for 10 minutes and the supernatant was discarded. The pellet was dissolved in 5 mL 0.1 M ammonium hydroxide and applied to a 30×400 mm column of DEAE-Sephadex in the acetate form. The column was eluted with 2 mL/min purified water with a linear gradient to 1 M acetic acid over 12 hours. Malonomicin containing fractions were located by monitoring the UV absorbance at 300 nm and by HPLC analysis. The malonomicin containing fractions were pooled and evaporated to dryness to yield 80 milligrams (mg) malonomicin (ESMS positive mode (M+H) 375).

II. Preparation of Compound II

A. Preparation of Intermediate Compound VII

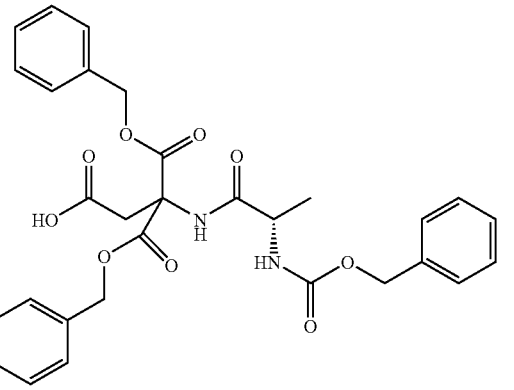

Compound VII

To a solution of $O^1$-benyzl $O^4$-t-butyl-2-benzyloxycarbonylaspartate (1.0 g, 2.4 millimole (mmol)) (produced by the process disclosed in J. L. van der Baan, J. W. F. K. Barnick and R. Bickelhaupt, Tetrahedron, 34, 223-231 (1978)) in dimethylformamide (DMF) (5 mL) was added L-N-benzyloxycarbonyl-alanine (L-Z-ala) (0.54 g, 2.4 mmol), 1-hydroxy-7-azabenzotriazole (HOAt) (0.35 g, 2.6 mmol) and 1-dimethylaminopropyl-3-ethyldicarbodiimide hydrochloride (EDCI) (0.56 g, 2.9 mmol). The mixture was cooled to 0° C. To the cold mixture was added diisopropylethylamine (0.54 mL, 3.1 mmol). The mixture was stirred without cooling overnight. The reaction mixture was diluted with water and extracted twice with ethyl acetate (EtOAc). The combined organic extracts were washed, sequentially, with 1N sodium hydrogen sulfate ($NaHSO_4$), 5 percent aqueous (aq.) sodium hydrogen carbonate ($NaHCO_3$) and brine, dried over sodium sulfate ($Na_2SO_4$) and concentrated to a yellow oil under reduced pressure. The oil was purified by silica gel chromatography using a mixture of EtOAc in pentane (5-15 percent) to yield 1.0 g of a pale yellow glass. This material (0.5 g, 0.8 mmol) was dissolved in dichloromethane (DCM) (3 mL) and treated with trifluoroacetic acid (3 mL). After 60 min. the mixture was evaporated under reduced pressure, redissolved in carbon tetrachloride (6 mL) and evaporated to yield VII as a pale yellow oil.

B. Preparation of Intermediate Compound VIII

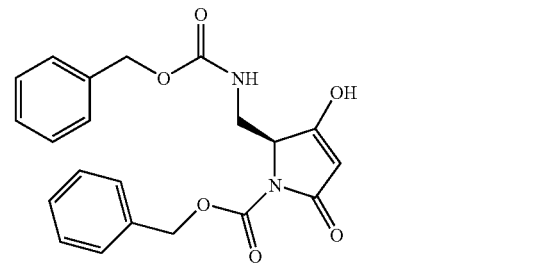

Compound VIII

To a solution of (2S)-2,3-bis{[(benzyloxy)carbonyl]amino}propanoic acid (3.72 g, 10.0), 4-dimethylaminopyridine (DMAP) (1.89 g, 15.5 mmol) and Meldrum's acid (1.73 g, 12.0 mmol) in DCM (60 mL) at 0° C. was added a solution of 1,3-dicyclohexylcarbodiimide (DCC) (1.0M in DCM, 11.5 mL plus 10 mL DCM) over 60 min. A fine precipitate formed during the addition. The mixture was held at 0° C. overnight. The mixture was filtered and the solid washed with DCM (30 mL). The filtrates were combined and washed with aq. $NaHSO_4$. The solution was dried over $Na_2SO_4$, filtered and concentrated at reduced pressure to yield a tan oil. This oil was dissolved in EtOAc (20 mL) and heated under reflux for 60 min. The mixture was cooled to room temperature and extracted three times with 5 percent $NaHCO_3$. The combined aqueous layers were extracted with ethyl ether ($Et_2O$), acidified to pH 2-3 and extracted with DCM. The combined DCM extracts were dried over $Na_2SO_4$, filtered and concentrated under reduced pressure to yield 4.3 g of a yellow oil. This oil was purified by silica gel chromatography (5 percent) methanol-95 percent chloroform-0.5 percent acetic acid) to yield 3.8 g of VIII as a pale tan oil.

C. Preparation of Compound II:

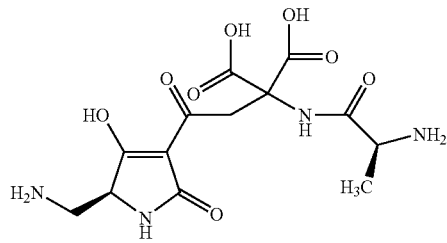

Compound II

To a solution of Compound VII (0.45 g, 0.80 mmol) and Compound VIII (0.32 g, 0.80 mmol) and DMAP (0.02 g, 0.16 mmol) in DCM at 0° C. was added (DCC) (1.0M solution in DCM, 0.88 mL, 0.88 mmol). The mixture was allowed to warm to room temperature. After 17 hours (h), additional DCC (0.88 mL, 0.88 mmol) and triethylamine (0.14 mL, 1.0 mmol) were added and the mixture stirred an additional 24 hours. The mixture was filtered, diluted with 1N $NaHSO_4$ and extracted with EtOAc. The combined organic phase was washed with saturated (sat.) sodium chloride, dried over $Na_2SO_4$ and concentrated under reduced pressure to yield a yellow oil. The oil was purified by silica gel chromatography (acetone 10-40 percent, 90-60 percent pentane with 1 percent acetic acid added) to yield a pale yellow oil (0.52 g). To a cold solution of this material in methanol (5 mL) was added Pearlman's catalyst (80 mg, 20 percent $Pd(OH)_2$ on carbon, 60 percent $H_2O$) and 4 drops of concentrated hydrochloric acid. The solution was placed under an atmosphere of hydrogen and stirred at 0° C. for 17 hours. The solution was made basic by addition of 6 drops of concentrated ammonium hydroxide and filtered through a pad of diatomaceous earth. The solids were extracted with water. The combined filtrates were evaporated to yield 0.11 g of the ammonium salt of compound II (ESMS positive mode (M+H) 358 and ESMS negative mode (M−H) 356, M−H$^+$—$CO_2$) 312) containing ammonium chloride and water.

III. Preparation of Compounds III, IV and V.

A. Preparation of Intermediate Compound IX:

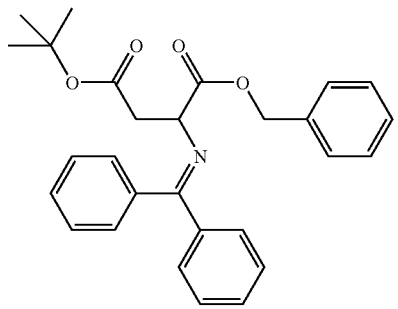

To a solution of benzyl [(diphenylmethylene)amino]acetate (produced by the process disclosed in M. J. McDonnell and R. L. Polt, *J. Org. Chem.*, 47, 2663-2666 (1982)) (3.29 g, 10.0 mmol) in tetrahydrofuran (THF) (40 mL) cooled to −77° C. was added a solution of sodium bis(trimethylsilyl)amide (1.0M in THF, 10.5 mL, 10.5 mmol) dropwise over 15 minutes while maintaining the temperature in the range of −75° to −77° C. The resulting lemon yellow solution was stirred at −77° C. for 10 minutes. t-Butyl bromoacetate (1.86 mL, 11.5 mmol) was added dropwise over 5 minutes. The mixture was allowed to slowly warm to 0° C. over 6.5 hours. Ice was added to quench the mixture. The mixture was diluted with sat. $NaHCO_3$ and partitioned between $Et_2O$ and additional sat. $NaHCO_3$. The $Et_2O$ layer was washed with dilute $NaHCO_3$, diluted with one fourth volume of n-pentane, washed with sat. aq. sodium chloride, dried over $Na_2SO_4$, filtered and concentrated under reduced pressure to yield 4.6 g of a yellow oil. The oil was purified by silica gel chromatography (10 percent EtOAc-90 percent cyclohexane) to yield 3.8 g of a pale yellow oil.

B. Preparation of Intermediate Compound X:

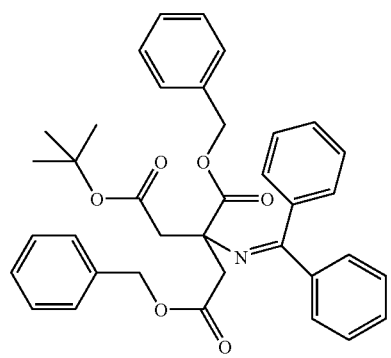

Compound X

Compound IX (4.40 g, 10 mmol) was dissolved in THF (50 mL) and cooled to −78° C. A solution of sodium bis(trimethylsilyl)amide (1.0 M in THF; 10 mL, 10 mmol) was added dropwise over 15 min. After an additional 10 min. at −78° C., the reaction flask was placed in an ice/water bath. After stirring 15 min. at 0° C., benzyl bromoacetate (2.39 g, 10.5 mmol) was added dropwise. During the addition, a precipitate formed. After 3 hours at 0° C., the reaction was quenched by addition of sat. aq. $NaHCO_3$ (50 mL), the layers were separated and the aq. layer was extracted with EtOAc three times (25 mL). The pooled organic fractions were washed sequentially with sat. aq. NaHCO$_3$ (50 mL) and brine (50 mL). The mixture was dried over Na$_2$SO$_4$, filtered and concentrated under reduced pressure to yield 5 g of crude product. This material was purified sequentially by flash chromatography (silica gel; 10 percent acetone/cyclohexane), centrifugal thin-layer chromatography (Chromatotron®, silica gel; 5 percent acetone/cyclohexane) and preparative reverse phase HPLC (Waters ODS-AQ 50×250 column; 90 percent acetonitrile/10 percent water buffered to pH 2 with 0.01 v/v H$_3$PO$_4$; flow rate 100 mL/min). Fractions containing product were pooled, concentrated under reduced pressure, neutralized with sat. aq. NaHCO$_3$, and extracted with DCM to provide 1.00 g of X.

C. Preparation of Intermediate Compound XI:

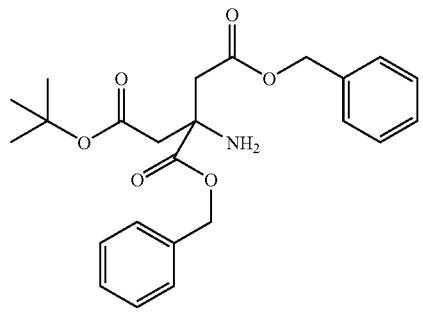

Compound XI

To a solution of Compound X (935 mg, 1.58 mmol) in THF (10 mL) was added a 15 percent aq. solution of citric acid (6 mL). The resulting turbid suspension was stirred at 25° C. for 47 hours. The reaction mixture was concentrated under reduced pressure, the aq. residue adjusted to pH 9 with aq. 1 N sodium hydroxide and extracted with Et$_2$O and DCM. The pooled organic fractions were washed with brine, dried over Na$_2$SO$_4$, filtered and concentrated under reduced pressure. The crude product was purified by flash chromatography (silica gel; EtOAc/cyclohexane) to provide 530 mg of XI.

D. Preparation of Intermediate Compounds XII and XIII:

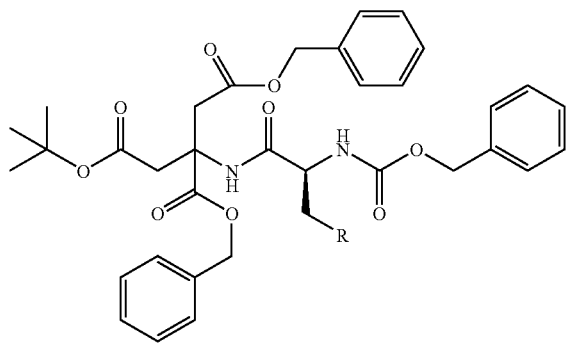

Compound XII, R = H
Compound XIII, R = OBn

Bn = benzyl

Compound XI (500 mg, 1.17 mmol) was reacted with O-benzyl-N-carbobenzoxy-L-serine (424 mg, 1.29 mmol), EDCI (280 mg, 1.46 mmol), HOAt (193 mg, 1.42 mmol) and diisopropylethylamine (189 mg, 1.46 mmol) in DMF (5 mL) at 25° C. After 93 hours, additional EDCI (40 mg) and O-benzyl-N-carbobenzoxyserine (85 mg) were added. After another 30 hours, the reaction mixture was partitioned between Et$_2$O (10 mL) and dilute aq. NaHSO$_4$ (5 mL). The aq. layer was extracted with Et$_2$O (10 mL), the pooled organic fractions were washed with dilute aq. NaHSO$_4$ (5 mL), diluted with ¼ volume pentane, washed with water (5 mL), 10 percent aq. NaHCO$_3$ (5 mL), brine (2×5 mL), dried over Na$_2$SO$_4$, filtered and concentrated under reduced pressure to provide 570 mg. The crude product was purified by flash chromatography (silica gel; 10 percent to 40 percent EtOAc/cyclohexane) to provide 530 mg of XIII as a mixture of diastereomers.

In the same manner as for the conversion of 2-amino-1,2,3-propanetricarboxylic acid, 2,3-bis(phenylmethyl)-1-(1,1-dimethylethyl) ester XI to XIII, XI (950 mg, 2.2 mmol) was reacted with N-carbobenzoxy-L-alanine (546 mg, 2.4 mmol) to provide 1.0 g of XII (mixture of diastereomers) as a sticky oil.

E. Preparation of Intermediate Compounds XIV and XV:

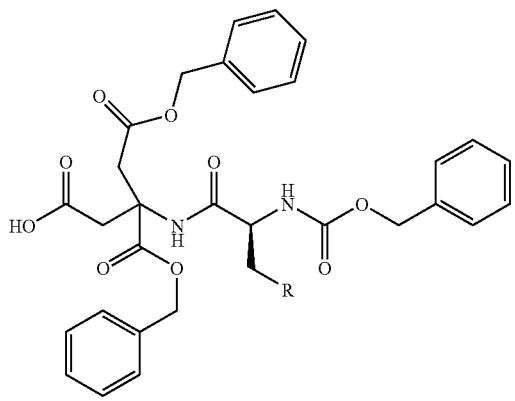

Compound XIV, R = H
Compound XV, R = OBn

Bn = benzyl

To a solution of XII (922 mg, 1.46 mmol) in DCM (5 mL) was added CF$_3$COOH (5 mL). After 48 hours, the reaction was concentrated under reduced pressure and the residue was partitioned between EtOAc (10 mL) and slightly alkaline brine (5 mL; pH adjusted with NaHCO$_3$, to neutralize residual CF$_3$COOH). The EtOAc layer was washed sequentially with water (5 mL) and brine (5 mL), then dried over Na$_2$SO$_4$, filtered and concentrated under reduced pressure to provide XIV (quantitative) as a sticky oil.

In the same manner as for the conversion of XII to XIV, XIII (480 mg, 0.6 mmol) was reacted with CF$_3$COOH to provide XV (373 mg) as a sticky oil.

F. Preparation of Intermediate Compounds XVI and XVII:

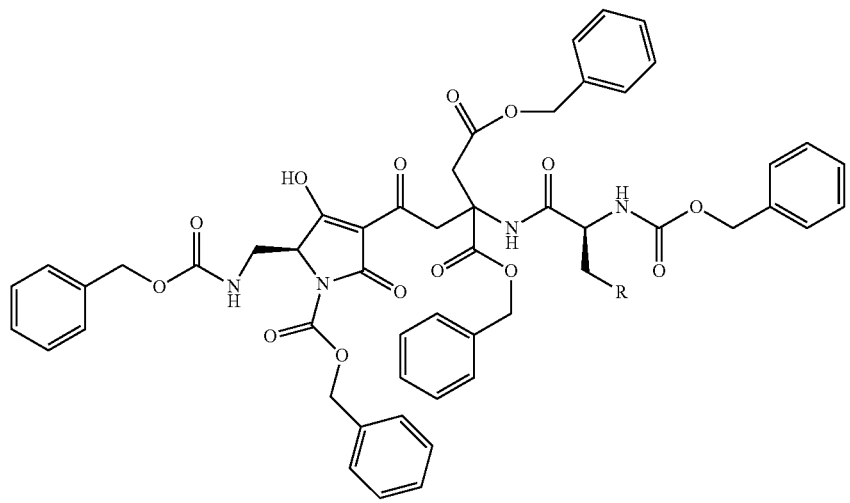

Compound XVI, R = H
Compound XVII, R = OBn

To a solution of XIV (730 mg, 1.3 mmol) in DCM (5 mL) was added Compound VII (527 mg, 1.3 mmol). To the cold mixture (0° C.) was added DMAP (31 mg, 0.25 mmol), triethylamine (154 mg, 1.5 mmol) and DCC (1.0 M solution in DCM, 1.4 mL; added over 5 min). After 10 min., the reaction was allowed to warm to 25° C. After stirring 24 hours, the reaction was filtered. The filter cake and filter paper were washed with DCM (3×5 mL), and the pooled filtrates were diluted with EtOAc (15 mL), washed with 10 percent aq. NaHSO$_4$ (15 mL) and brine (15 mL), dried over Na$_2$SO$_4$, filtered and concentrated under reduced pressure. The crude product was purified by preparative HPLC (Waters ODS-AQ 50×250 column; 90 percent acetonitrile/10 percent water buffered to pH 2 with 0.01 v/v H$_3$PO$_4$; flow rate 100 mL/min). Fractions containing product were pooled, partially concentrated under reduced pressure, neutralized with sat. aq. NaHCO$_3$, and extracted into DCM and EtOAc dried over Na$_2$SO$_4$, filtered and concentrated under reduced pressure to provide XVI (300 mg).

In the same manner as for the conversion of XIV to XVI, XV (250 mg, 0.37 mmol) was converted to XVII (111 mg).

G. Preparation of Compounds III/IV and V/VI:

Compound V

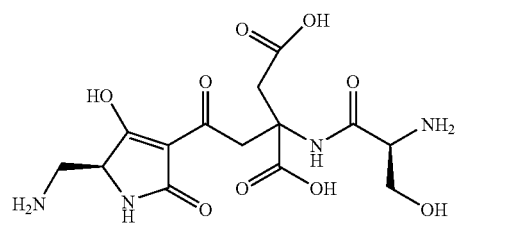

-continued

Compound VI

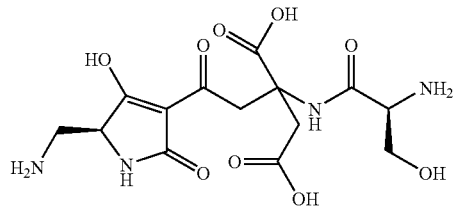

Compound III

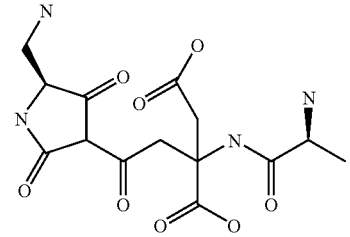

Compound IV

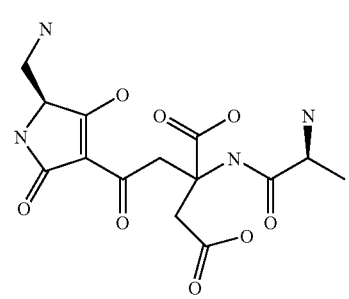

To a solution of Compound XVII in methanol (5 mL) and DCM (5 mL) at 0° C., was added Pearlman's catalyst (50 mg, 20 percent Pd(OH)$_2$ on carbon, 60 percent H$_2$O) and 2 drops of concentrated hydrochloric acid. The solution was placed under an atmosphere of hydrogen and stirred at 0° C. for 6 days. After addition of more Pearlman's catalyst (50 mg) the reaction was stirred for another 48 hours. The reaction mixture was filtered through a Celite/cotton plug and concentrated under reduced pressure. The residue was purified by HPLC (HILIC Column Polyhydroxyethyl A (Poly LC, Inc., Columbia, Md.) 250×21.0 mm, 5 micron particles, 300 Angstrom pores, Item 2521H40503; 10 mL/min; gradient 60 to 40 percent acetonitrile in 0.01 M ammonium acetate from 2 to 22 min) to provide V (14 mg; ESMS positive mode, 389 (M+H)) and VI (2-epi-V; 11 mg, ESMS positive mode, 389 (M+H)).

In the same manner as for the conversion of XVII to IV, XVI (30 mg, 0.03 mmol) was converted to III (1.5 mg; ESMS positive mode, 373 (M+H)) and IV (1.3 mg ESMS positive mode, 373 (M+H)). The reaction mixture was filtered through a Celite/cotton plug and rotary evaporated. The residue was purified by HPLC (HILIC Column Polyhydroxyethyl A (Poly LC, Inc., Columbia, Md.) 250×21.0 mm, 5 micron particles, 300 Angstrom pores, Item 2521H40503; 10 mL/min; gradient 45 to 20 percent acetonitrile in 0.01 M ammonium acetate from 2 to 22 min).

Biological Testing

Compound Formulation for Protectant Examples

Compound formulation was accomplished by dissolving Compound I, II, III, IV, V, or VI in water with serial dilutions to obtain desired rates. Final treatment volumes were obtained by adding 0.1 percent aqueous Ethomeen T25 or 0.1 percent aqueous Spraymate X77+0.1 percent wt./vol. ammonium sulfate$^+$.

One Day (24 Hour) Protectant (1 DP)

Downy Mildew of Grape (*Plasmopara viticola*-PLASVI) (1 DP)

Vines (cultivar Carignane) were grown from seed in a soilless peat-based potting mixture "Metro-Mix 360" (W.R Grace and Co.) until the seedlings were 10-20 cm tall. These plants were then sprayed to runoff with the test compound at a rate of 200 ppm. After 24 hours the test plants were inoculated by spraying with an aqueous sporangia suspension of *Plasmopara viticola* (PLASVI). The plants were then transferred to a dew chamber for 24 hours, then to the greenhouse until disease developed on the untreated control plants.

Late Blight of Tomato (*Phytophthora infestans*-PHYTIN) (1 DP)

Vines (cultivar rutgers) were grown from seed in a soil-less peat-based potting mixture "Metro-Mix 360" (W.R Grace and Co.) until the seedlings were 10-20 cm tall. These plants were then sprayed to runoff with the test compound at a rate of 200 ppm. After 24 hours the test plants were inoculated by spraying with an aqueous sporangia suspension of *phytophthora infestans* (PHYTIN). The plants were then transferred to a dew chamber for 24 hours, then to the greenhouse until disease developed on the untreated control plants.

Brown Rust of Wheat (*Puccinia recondita* f. sp. *tritici*-PUCCRT) (1 DP)

Wheat (cultivar Monon) was grown in plastic pots (6.2 cm×8.75 cm) containing 50 percent mineral soil, 50 percent Metro-Mix 360 (W.R Grace and Co.) until the seedlings were 10-20 cm tall. These plants were then sprayed to runoff with the test compound at a rate of 200 ppm. After 24 hours the test plants were inoculated by spraying with an aqueous spore suspension of *Puccinia recondita* f. sp. *tritici* (PUCCRT). The plants were then transferred to a dew chamber for 24 hours, then to the greenhouse until disease developed on the untreated control plants.

Glume Blotch of Wheat (*Leptosphaeria nodorum*-LEPTNO) (1 DP)

Wheat (cultivar Yuma) was grown in plastic pots (6.2 cm×8.75 cm) containing 50 percent mineral soil, 50 percent Metro-Mix 360 (W.R Grace and Co.). until the seedlings were 10-20 cm tall. These plants were then sprayed to runoff with the test compound at a rate of 200 ppm. After 24 hours the test plants were inoculated by spraying with an aqueous spore suspension of *Leptosphaeria nodorum* (LEPTNO). The plants were then transferred to a dew chamber for 24 hours, then to the greenhouse until disease developed on the untreated control plants.

Speckled Leaf Blotch of Wheat (*Septoria tritici*-SEPTTR) (1 DP)

Wheat (cultivar Monon) was grown in plastic pots (6.2 cm×8.75 cm) containing 50 percent mineral soil, 50 percent Metro-Mix 360 (W.R Grace and Co.) until the seedlings were 10-20 cm tall. These plants were then sprayed to runoff with the test compound at a rate of 200 ppm. After 24 hours the test plants were inoculated by spraying with an aqueous spore suspension of *Septoria tritici* (SEPTTR). The plants were then transferred to a dew chamber for 24 hours, then to the greenhouse until disease developed on the untreated control plants.

Powdery Mildew of Wheat (*Erysiphe graminis* f. sp. *tritici*-ERYSGT) (1 DP)

Wheat (cultivar Monon) was grown in plastic pots (6.2 cm×8.75 cm) containing 50 percent mineral soil, 50 percent Metro-Mix 360 (W.R Grace and Co.) until the seedlings were 10-20 cm tall. These plants were then sprayed to runoff with the test compound at a rate of 200 ppm. After 24 hours the test plants were inoculated with *Erysiphe graminis* f. sp. *tritici* (ERYSGT) by dusting spores from stock plants onto the test plants. The plants were then transferred to the greenhouse until disease developed on the untreated control plants.

Apple Scab (*Venturia inaequalis*-VENTIN) (1 DP)

Apples were grown in plastic pots (6.2 cm×8.75 cm) containing 100 percent Metro-Mix 360 (W.R Grace and Co.) until the seedlings were 10-20 cm tall. These plants were then sprayed to runoff with the test compound at a rate of 200 ppm. After 24 hours the test plants were inoculated with conidia that were previously harvested (up to 6 months earlier) by washing infected leaves in deionized water and then freezing the solution at a concentration of 400,000 spores/ml. The plants were then transferred to a dew chamber for 24 hours, then to the greenhouse until disease developed on the untreated control plants (8 days). Disease severity was evaluated only on the two youngest leaves at the time of inoculation because older leaves become highly resistant to infection with this pathogen.

Cucumber Anthracnose (*Colletotricum lagenarium*; COLLLA) (1 DP)

Cucumber plants (variety Bush Champion) were grown in plastic pots containing 100 percent Metro-Mix 360 (W.R Grace and Co.) until the first true leaf was 20-80 percent expanded. Each pot contained 1 seedling. These plants were then sprayed to runoff with the test compound at a rate of 200 ppm. After 24 hours, the plants were sprayed with an aqueous spore suspension of *Colletotricum lagenarium* (COLLLA). The plants were then transferred to a dew chamber for 24 hours, then to a growth chamber until disease developed on the untreated control plants.

The following TABLE I. presents the activity of typical compound(s) of the present invention when evaluated in these experiments.

| Compound | PLASVI | PHYTIN | PUCCRT | LEPTNO | SEPTTR | ERYSGT | VENTIN+ | COLLLA |
|---|---|---|---|---|---|---|---|---|
| I | ++ | ++ | ++ | + | ++ | − | +, ++ᵉ, ++ᵅ | − |
| II | − | + | ++ | − | + | − | | |
| III* | | | + | | | | | |
| IV* | | | + | | | | | |
| V | | + | ++ | − | − | − | | |
| VI | | − | ++ | − | + | − | | | blank space = not tested
− = 0-29 percent control of plant disease
+ = 30-74 percent control of plant disease
++ = 75-100 percent control of plant disease
rate = 200 ppm
*Drop Line Test 0.5 µg/leaf
+0.1 percent aqueous Spraymate X77 + 0.1 percent wt./vol. ammonium sulfate in final treatment volume.
ᵉ50 ppm and 100 ppm
ᵅCurative at 200 ppm (compound was added 2 days after inoculation)

In Example 3, a Drop Line Test was used, wherein instead of spraying the plant to runoff, a 2 microliter drop was placed on the wheat leaf and observed for disease control.

Curative Testing for Compound I

Plant fungal pathogens and their hosts used in this study are listed in TABLE II. Tomatoes and grapes were grown in a soil-less peat-based potting mixture (Metro-Mix 360) while wheat was propagated in a 50/50 mix of mineral soil and Metro-Mix 360.

TABLE II

Host plants, common disease names, causal fungal pathogens, and their Bayer codes used in this study.

| Host name (variety) | Disease name | Pathogen |
|---|---|---|
| Wheat (Monon) | Brown rust | *Puccinia recondita* f. sp. *tritici* PUCCRT |
| Wheat (Monon) | Leaf blotch | *Septoria tritici* SEPTTR |
| Tomato (Rutgers) | Late blight | *Phytophthora infestans* PHYTIN |

Compound Formulation for Curative Examples

The malonomicin sample (Compound I) used in the low volume foliar spray was prepared by dissolving the material in deionized water with the desired adjuvant concentration. (0.05 percent Spraymate X-77+0.05 percent PVA+0.1 percent ammonium sulfate+0.1 percent EDTA)

For low volume applications, compound was applied to plants at the spray volume of 300 L/ha using a track sprayer with an SS8003E spray nozzle and a spray pressure of 255 kPa with a boom height of 40 cm from test plants. For a control, the same mixture is sprayed without active ingredient (solvent control).

Test Descriptions

Curative tests (DC) were inoculated the designated day(s) prior to treatment application. Disease severity was assessed as the percentage of the total surface area of the sprayed leaves covered by disease. Percent disease control relative to the solvent control was then calculated. Phytotoxicity symptoms and severity, if present, were also recorded. Four replicate plants per treatment for low volume applications were used.

Inoculation

PUCCRT

Wheat plants were inoculated using approximately $1.2 \times 10^6$ urediospores/mL or 0.3 g urediospores/100 mL of water. Tween 20 was added to the spores to make a paste (7 drops per 0.3 g spores). The spore/Tween 20 mixture was gradually liquefied with deionized water to the desired volume. The spore suspension was then filtered through 2 layers of cheesecloth. Inoculated plants were placed into a walk-in dew room at 22° C., 99 percent relative humidity (RH) for 12-15 hours. The test plants were then moved and maintained in a greenhouse at 20-22° C. until disease was fully expressed on the solvent control, typically seven days.

SEPTTR

Wheat plants were inoculated using approximately $1 \times 10^7$ spores/mL. Distilled water was poured into inoculum plates and the spores were dislodged using a spatula. The spores and water were filtered through 2 layers of cheesecloth, and three drops of Tween 20 per 100 mL of solution were added as a wetter. Test plants were then placed in a walk-in dew room at 22° C., 99 percent RH for 24 hours, after which time the plants were sub-irrigated with Hoagland's solution for 30 minutes and then moved into a misting greenhouse system where they were lightly misted every 90 seconds for three days. When the three-day misting period was completed, the plants were moved to the dry area of the greenhouse and bottom-watered daily until disease was fully expressed on the solvent control (10-14 days in summer, 14-21 days in winter). During the fall and winter months, the addition of a cart hood was used post-dew room, until assessment, in order to enhance disease uniformity and expression.

PHYTIN

Spore suspension was prepared by washing the surface of rye seed agar plate cultures, which were between 2 and 3 weeks old, with cold (4° C.) deionized water. Flooded plates were rubbed with a plastic cell spatula to release sporangia. The suspension was filtered through two layers of cheesecloth to remove mycelia, and adjusted to a final concentration of $5 \times 10^4$ spores/mL. The inoculum was then sprayed onto tomato plants with uniform droplets on the leaf surface one day prior to treatment with active ingredient. The inoculated plants were kept overnight in a dew chamber at 20° C. to initiate infection. The seedlings were then sprayed with active ingredient and moved to a 20° C. growth room to allow disease symptoms to fully develop on solvent control plants, which took 4-5 days.

TABLE III

| | | Percent disease control by malonomicin (Compound I) in a curative low volume test. | | | |
|---|---|---|---|---|---|
| Compound | Rate (g ai/ha) | PUCCRT 1DC | PUCCRT 3DC | SEPTTR 3DC | PHYTIN 1DC |
| 1 | 250 | ++ | ++ | ++ | ++ |
| | 125 | ++ | ++ | ++ | + |
| | 62.5 | + | ++ | ++ | − |
| | 31.2 | + | ++ | ++ | + |
| | 15.6 | − | + | ++ | + |
| | 7.8 | − | − | ++ | − |

− = 0-29 percent control of plant disease
+ = 30-74 percent control of plant disease
++ = 75-100 percent control

What is claimed is:

1. A method of controlling fungal attack comprising applying to the soil, plant, roots, foliage, seed or locus of a fungi, or to a locus in which infestation of fungi is to be prevented, a fungicidal effective amount of one or more compounds of the formula

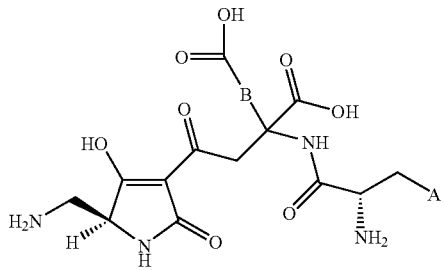

Formula I wherein B is defined as either a bond or an alkylene group, and A is defined as either OH or H.

2. The method of claim 1, wherein A is OH.
3. The method of claim 1, wherein B is a bond.
4. The method of claim 1, wherein A is OH and B is a bond.

* * * * *